United States Patent [19]
Bliesener et al.

[11] Patent Number: 4,718,936
[45] Date of Patent: Jan. 12, 1988

[54] 6-(3-THIENYLMETHYLAMINO)-PURINE, ITS PREPARATION AND ITS USE

[75] Inventors: Jens-Uwe Bliesener, Deidesheim; Hubert Sauter, Mannheim; Norbert Goetz, Worms; Johann Jung, Limburgerhof; Klaus Grossmann, Neuhofen, all of Fed. Rep. of Germany

[73] Assignee: BASF Aktiengesellschaft, Ludwigshafen, Fed. Rep. of Germany

[21] Appl. No.: 711,205

[22] Filed: Mar. 13, 1985

[30] Foreign Application Priority Data

Mar. 14, 1984 [DE] Fed. Rep. of Germany ....... 3409272

[51] Int. Cl.⁴ .................... C07D 473/26; A01N 43/90
[52] U.S. Cl. ....................................... 71/92; 544/276; 544/277; 71/88
[58] Field of Search ................... 544/276, 277; 71/88, 71/92

[56] References Cited
PUBLICATIONS

R. Wegler, Chemie der Pflanzenschutz-und Schädlingsbekämpfungsmittel, vol. 4, pp. 28-32 (Berlin 1977).
Phytochemistry, 16 (1977), p. 1865.

Primary Examiner—Nicholas S. Rizzo
Attorney, Agent, or Firm—Keil & Weinkauf

[57] ABSTRACT 6-(3-Thienylmethylamino)-purine of the formula

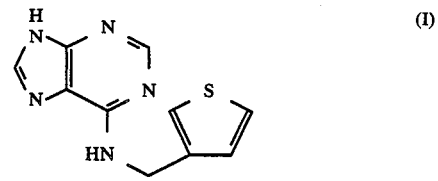

a process for its manufacture, and agents for regulating plant growth containing a compound of the formula I.

4 Claims, No Drawings

6-(3-THIENYLMETHYLAMINO)-PURINE, ITS PREPARATION AND ITS USE

The present invention relates to the novel compound 6-(3-thienylmethylamino)-purine (also referred to as thenylaminopurine) of the formula I, a process for its preparation and its use for regulating plant growth.

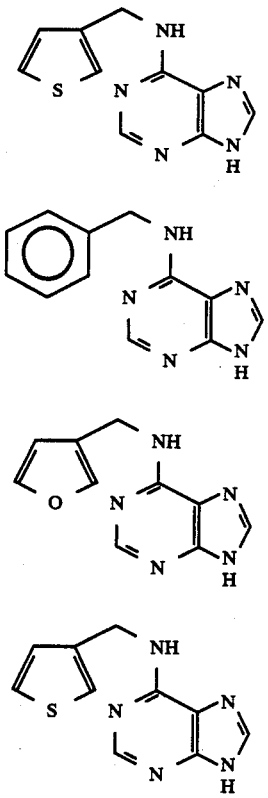

It is known that 6-benzylaminopurine of the formula II (benzyladenine) influences plant growth in a similar manner to the natural phytohormone 6-(2-furylmethylamino)-purine of the formula III (kinetin) (cf. for example Wegler, Chemie der Pflanzenschutz-und Schädlingsbekämpfungsmittel).

Examples of the physiological actions are the control of growth by cell division in callus tissues and intact plants, the promotion of bud and flower formation, the stimulation of seed germination, the overcoming of dormant phase of seeds, storage organs and buds, the promotion of sideshoot formation, and the retardation of the ageing processes in plants.

These actions are referred to as cytokinin-like actions.

6-(2-Thienylmethylamino)-purine of the formula IV also exhibits cytokinin-like actions, but these are less pronounced than those of benzyladenine of the formula II (Phytochemistry 16, (1977), 1865).

It is an object of the present invention to provide active ingredients whose action is superior to that of the conventional adenine derivatives.

We have found that this object is achieved, and that the 6-(3-thienylmethylamino)-purine of the formula I, which is isomeric with IV, possesses outstanding plant growth-regulating properties, which are also superior to those of benzyladenine.

The active ingredient (I) according to the invention can be prepared, for example, by subjecting 6-aminopurine to reductive alkylation with thiophene-3-aldehyde in the presence of formic acid. Another possible method of preparation comprises first acylating 6-aminopurine with thiophene-3-carbonyl chloride and then reducing the product to the compound of the formula I. Other possible methods of preparation depend on, inter alia, the availability of appropriate raw materials; the achievable yields or the costs for the industrial-scale preparation process may also vary. It is therefore advisable to carry out an investigation using the conventional means of physical chemistry and of process engineering.

For the first-mentioned version of the process, 1 mole equivalent of adenine is heated with from 1 to 50, preferably from 2 to 20, mole equivalents of formic acid and with from 0.5 to 2, preferably from 0.9 to 1.2, mole equivalents of thiophene-3-aldehyde, advantageously in the presence of a solvent, at about 90°-120° C. (eg. under reflux). The crude mixture is worked up and purified in a conventional manner, for example by distilling off excess reagents, extractive purification steps and, if required, recrystallization, for example as described in Example 1.

EXAMPLE 1

Preparation of 6-(3-thienylmethylamino)-purine; version A 405 g (3 moles) of adenine are dissolved in 1,700 ml (45 moles) of formic acid, while cooling with ice, 504 g (5.4 moles) of thiophene-3-aldehyde are added, and the mixture is refluxed for 15 hours. The excess formic acid is then slowly distilled off in the course of 8 hours, the temperature increasing to about 180° C. toward the end. After cooling, 1.5 l of 25% strength aqueous sodium hydroxide solution are added to the residue, and the mixture is stirred overnight. Thereafter, undissolved substances are filtered off, the filtrate is extracted with 3×1 l of dichloromethane, the aqueous phase is brought to pH 8-9 with 10% strength hydrochloric acid, the desired product being precipitated. When the product is filtered off, washed with water and dried at 60° C. under reduced pressure, 687 g of 6-(3-thienylmethylamino)-purine of melting point 227°-229° C. are obtained.

In the other version of the process, 1 mole equivalent of adenine is heated in a conventional manner (Phytochemistry 16, (1977) 1865) with from 1 to 10, preferably from 2 to 5, mole equivalents of thiophene-3-carbonyl chloride in the presence of a proton acceptor (e.g. pyridine), possibly in a solvent, such as dioxane, at as high as 200° C., and the mixture is worked up in a conventional manner and if necessary recrystallized, for example as described above.

The reduction of the resulting 6-(3-thenoylamino)purine (also referred to as thienylcarbonylaminopurine) can be carried out in a conventional manner, for example in a solvent at as high as 200° C., preferably from 50° to 100° C., using a reducing agent (eg. diborane in the presence of a Lewis acid or Lithium aluminum hydride), and the mixture can be worked up in the usual manner. The reduction with lithium aluminum hydride in tetrahydrofuran takes place particularly smoothly, for example as described in Example 2 b.

EXAMPLE 2

Preparation of 6-(3-thienylmethylamino)-purine; version B (a) 62.6 g (0.439 mole) of thiophene-3-carbonyl chloride are added to a suspension of 19.7 g (0.146 mole) of adenine in 100 ml of dry pyridine. The mixture is refluxed for 10 hours, the pyridine is distilled off, the residue is taken up in chloroform, the solution is washed with dilute sodium bicarbonate solution and dried over sodium sulfate, and the solvent is then stripped off in a rotary evaporator. The solid residue is stirred repeatedly with cyclohexane and then recrystallized from ethanol and dried at about 40° C. under reduced pressure. 6-(3-Thenoylamino)-purine is obtained in a yield of 60%.

(b) A suspension of 20 g (0.082 mole) of 6-(3-thenoylamino)-purine in 1 l of absolute tetrahydrofuran is added dropwise to a stirred suspension of 6.5 g (0.17 mole) of lithium aluminum hydride in 350 ml of absolute tetrahydrofuran at 80° C. After 3 hours, the excess hydride is decomposed with sodium sulfate decahydrate, the residue is filtered off, the filtrate is brought to dryness and the resulting oily crystal slurry is crystallized several times from tetrahydrofuran. 6-(3-Thienylmethylamino)-purine is obtained in a yield of 25%.

The novel active ingredient affects plant metabolism and may therefore be used as a growth regulator.

It is known from experience that a growth-regulating active ingredient may have one or several different actions on plants.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation of the active ingredient; and
(g) the concentration at which the active ingredient is applied.

At all events, the aim with growth regulators is to have a positive influence on crop plants.

A description of some of the various possibilities of using the growth regulator according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

A further mechanism for increasing yields with growth regulators is based on the fact that the nutrients are employed to a greater extent for blossom and fruit formation, whereas vegetative growth is restricted. Because the leaf or plant mass is relatively low, this also counteracts attack by various, particularly fungal, diseases.

The inhibition of vegetative growth also makes closer planting possible in numerous crops, which means an increase in yield based on the area cropped. The compounds according to the invention are particularly suitable for suppressing vegetative growth in crop plants such as soybeans, sunflowers, groundnuts, rape, ornamentals, cotton, rice and grasses.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of trees.

The action of the novel compound is superior to that of prior art growth regulators. This action is manifested not only in monocotyledon crops, e.g., cereals such as wheat, barley, rye, oats and rice or Indian corn or grasses, but also particularly in dicotyledons (e.g., sunflowers, tomatoes, groundnuts, grapes, cotton, rape and, particularly, soybeans) and various ornamentals such as chrysanthemums, poinsettias and hibiscus.

The active ingredient may be applied to the crop either by treating the seed, treating the soil, or by spraying the leaves.

Because the active ingredient is well tolerated by the crop plants, application rates may vary within a wide range.

When the active ingredient is used to treat seed, active ingredient amounts of from 0.001 to 50 g, preferably from 0.01 to 10 g, per kg of seed are generally required.

When the active ingredient is applied to the soil or foliage, amounts of from 0.001 to 12 kg/ha, preferably from 0.01 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, ketones, e.g. cyclohexanone, dimethylformamide, and water; solid carriers, for example natural rock powders, e.g. kaolin, alumina, talc and chalk, and synthetic rock powders, e.g. highly disperse silica and silicates; emulsifiers, and other surfactants, for example non-ionic and anionic emulsifiers, e.g. polyoxyethylene fatty alcohol ethers and alkylsulfonates, and dispersants, for example lignin, sulfite waste liquors and methylcellulose. It is preferred to use the compound according to the invention in aqueous solution, if desired with the addition of water-miscible organic solvents such as methanol or other lower alcohols, acetone, dimethylformamide or N-methylpyrrolidone. The formulations in general contain from 0.1 to 95% by weight of active ingredient, preferably from 0.5 to 90%.

The formulations may be applied at any time—preemergence, postemergence, or as seed disinfectants.

The following examples demonstrate the action of the active ingredient as a growth regulator, without excluding the possibility of its being used in another way.

EXAMPLE 1

Increase in the green weight of radish cotyledons (after Letham 1971, Physiol. Plant 25, 391–396)

The external cotyledon of uniform-size, freshly germinated radish seeds ("Karissima GS" variety) was harvested. 6 cotyledons were incubated in Petri dishes 5 cm in diameter with 2 ml of 1 mmole potassium phosphate buffer (pH 6.0) containing the candidate sample. After a 72-hour incubation period at 25° C. in the dark, the increase green weight of the cotyledons was determined as a measure of the effectiveness of the growth regulators. Table 1 contains average values from parallel batches.

TABLE 1

| | Increase in green weight (in %) over the control | | | |
|---|---|---|---|---|
| Molar conc. | 6-(3-thienyl-methylamino)-purine | benzyl-adenine | kinetin | isopentenyl-adenine |
| $10^{-4}$ | 262 | 236 | 200 | 227 |
| $10^{-5}$ | 220 | 203 | 207 | 142 |
| $10^{-7}$ | 189 | 185 | 151 | 82 |

It will be apparent from these figures that treatment of radish cotyledons with the agent according to the invention results in greater green weight increases than treatment with prior art growth regulators having a cytokinin-like action.

EXAMPLE 2

Induction of bud formation in Funaria prothallia (Han and Bopp 1968, Planto 83, 115–118)

Spore capsules of the moss Funaria hygrometrica (L.) Sibth. were opened under aseptic conditions, and protonema cultures were grown from the individual spores on the surface of a Knop agar at 21° C. and a light intensity of 2,000 lux. After 4 to 5 days, individual protosemata were isolated and transferred to a new Petri dish with Knop agar covered with a cellophane layer. After a further 8 to 11 days, 10 caulonema filaments were isolated and laid in rows on the cellophane surface. The strips were cut and transferred to agar plates with added active ingredient. After 2 to 3 days the number of induced buds on the caulonema filaments was determined as a measure of the cytokinin-like action of the growth regulators (Table 2).

TABLE 2

| | Number of induced buds compared with control | | | |
|---|---|---|---|---|
| Molar conc. | 6-(3-thienyl-methylamino)-purine | benzyl-adenine | kinetin | isopentenyl-adenine |
| $10^{-4}$ | 62 | 38 | 34 | — |
| $10^{-5}$ | 60 | 43 | 8 | 37 |

Table 2 shows that the agent according to the invention induces by far the largest number of new buds.

EXAMPLE 3

Inhibition of leaf ageing in barley (Grossmann and Jung 1982, Z. Acker-und Pflanzenbau, 151, 149–165)

The plants employed were 12- to 14-day old barley plants (summer barley, "Union" variety) grown under greenhouse conditions. The first true leaf was detached and cut up into 1 cm long segments. Six segments were placed in a sterile Petri dish 4 cm in diameter containing 2 ml of sterile distilled water and varying additions of active ingredients. After a 3-day incubation period at 25° C. in the dark, the leaf segments from the parallel batches were combined and pounded in a shallow mortar under liquid $N_2$. 1 ml of 25 mmole tris HCl buffer (pH: 7.5) and a spatula tip of Kollidon were added to the homogenate, and the mixture was briefly centrifuged. The supernatant liquid was used to determine the soluble protein content via complex formation with the dye Coomassie Brilliant Blue G 250 and photometric evaluation at 595 nm. The chlorophyll content of the leaf segments was determined by photometric evaluation at 652 nm of the methanolic extracts of the sediment (Table 3).

TABLE 3

| Compound ($10^{-4}$ M) | 6-(3-thienyl-methylamino)-purine | benzyl-adenine | kinetin | isopentenyl-adenine |
|---|---|---|---|---|
| Chlorophyll content | 170 | 165 | 154 | 160 |
| Protein content | 140 | 125 | 130 | 133 |

Figures in % of the control.

Table 3 shows that the agent according to the invention significantly inhibits the decomposition both of chlorophyll and of the soluble protein of the barley leaf segments.

EXAMPLE 4

Induction of lateral branching in *Vicia faba*

8-day old broad bean seedlings ("Herra" variety) were grown under greenhouse conditions and then kept hydroponically. Foam was wrapped round the root collars of the seedlings, which were then fitted into openings in the lids of cylindrical plastic vessels (4 liters in volume). The nutrient solution according to Linsmaier and Skoog (1946), Physiol. Plant. 18, 100–127) contained the individual active ingredients in the concentrations given below. After 4 weeks the number of induced lateral shoots was determined as a measure of the cytokinin-like action of the growth regulators (Table 4).

TABLE 4

| Molar conc. | No. of lateral shoots per 5 plants | | | |
|---|---|---|---|---|
| | 6-(3-thienyl-methylamino)-purine | benzyl-adenine | kinetin | control |
| $10^{-5}$ | 7 | 3 | 1 | 0 |
| $10^{-6}$ | 3 | 1 | 0 | 0 |

Table 4 shows that by far the most lateral shoots were induced with the agent according to the invention, which points to a significant reduction in apical dominance of the broad bean plants caused by the agent according to the invention.

EXAMPLE 5

Reduction in soybean growth height 8-day old soybean seedlings ("Gieso" variety) were grown under greenhouse conditions and then kept hydroponically. The nutrient solution according to Linsmaier and Skoog contained the individual active ingredients in the concentrations given below. After 3 weeks the growth-regulating action observed was confirmed by measurements of the growth height. The figures obtained were compared with those for the untreated plants (control).

Not only was growth height reduced—the intensity of leaf color rose too. The increased chlorophyll content is indicative of a higher rate of photosynthesis, so that higher yields can be expected.

The figures obtained are given in Table 5.

TABLE 5

| Molar conc. | Growth height (in % of control) | | |
|---|---|---|---|
| | 6-(3-thienyl-methylamino)-purine | benzyl-adenine | kinetin |
| $10^{-5}$ | 48 | 40 | 54 |
| $10^{-6}$ | 47 | 54 | 72 |

Table 5 shows that the agent according to the invention effects the greatest reduction in soybean plant growth height.

We claim:

1. 6-(3-Thienylmethylamino)-purine of the formula

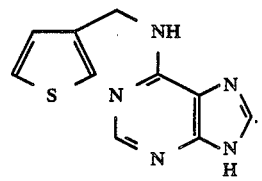

(I)

2. A composition for regulating plant growth which comprises: an effective plant growth regulating amount of a compound as set forth in claim 1 and a solid or liquid carrier.

3. A method of regulating plant growth, wherein an effective amount of a compound as set forth in claim 1 is allowed to act on plant seed, or plants or their habitat.

4. The composition of claim 2, which further contains one or more surfactants.

* * * * *